US007053625B2

(12) United States Patent
Dominelli et al.

(10) Patent No.: US 7,053,625 B2
(45) Date of Patent: *May 30, 2006

(54) METHOD AND APPARATUS FOR DETECTING WEAR IN COMPONENTS OF HIGH VOLTAGE ELECTRICAL EQUIPMENT

(75) Inventors: Nicola Dominelli, Coquitlam (CA); Hans Schellhase, Delta (CA); David W. Casson, Langley (CA); Edward A. Hall, Delta (CA)

(73) Assignee: Electric Power Research Institute, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/917,747

(22) Filed: Aug. 13, 2004

(65) Prior Publication Data

US 2005/0104598 A1 May 19, 2005

Related U.S. Application Data

(63) Continuation-in-part of application No. 10/241,108, filed on Sep. 11, 2002, now Pat. No. 6,777,948.

(51) Int. Cl.
*G01N 27/60* (2006.01)

(52) U.S. Cl. ..................... 324/455; 324/456
(58) Field of Classification Search ............ None
See application file for complete search history.

(56) References Cited

U.S. PATENT DOCUMENTS 3,164,006 A * 1/1965 Alburger ............... 73/53.01

| 3,715,598 | A | 2/1973 | Tomlin, Jr. |
| 5,389,792 | A | 2/1995 | DiMarzio et al. |
| 5,453,591 | A | 9/1995 | Stroud |
| 5,844,331 | A | 12/1998 | Kieser et al. |
| 6,023,036 | A | 2/2000 | Nichols |
| 6,448,758 | B1 * | 9/2002 | Krahn et al. ............ 324/158.1 |
| 6,777,948 | B1 * | 8/2004 | Dominelli et al. ......... 324/455 |

FOREIGN PATENT DOCUMENTS

JP 7-333369 * 12/1995

OTHER PUBLICATIONS

Evident Technologies, "Quantum Dot Material Systems—Introduction", (2003-2005)<http://evidenttech.com/products/evidots/quantum-dot-introduction.php>.
Evident Technologies, "Quantum Dot Specification", (Apr. 27, 2005)<http://evidenttech.com/products/evidots/quantum-dot-specification.php>.

(Continued)

*Primary Examiner*—Vincent Q. Nguyen
(74) *Attorney, Agent, or Firm*—Morgan, Lewis & Bockius LLP (57) ABSTRACT

A tracer material is embedded in a component of electrical equipment to detect excessive wear of the component when it is exposed to an electrical arc. As the component wears, the tracer material becomes exposed to the electrical arc and emits electromagnetic radiation, which is monitored continuously. The tracer material is selected so that it emits electromagnetic radiation when it is exposed to an electrical arc that is distinct from electromagnetic radiation emitted by any other parts of the component. A fluorescent tracer material may also be used.

28 Claims, 11 Drawing Sheets

OTHER PUBLICATIONS

Evident Technologies, "Quantum Dot Emission and Absorption Spectra", (2003-2005)<http://evidenttech.com/products/evidots/quantum-dot-emission-absorption.php>.

Evident Technologies, "Quantum Dot Emission and Absorption Spectra", (2003-2005)<http://evidenttech.com/products/evidots/quantum-dot-emission-absorption.php>.

Evident Technologies, "Quantum Dot Test Kits with EviDots", (2003-2005)<http://evidenttech.com/products/evidots/quantum-dot-kits-and-products.php>.

Evident Technologies, "Quantum Dot Product Features", (2003-2005)<http://evidenttech.com/products/evidots/quantum-dot-product-features.php>.

* cited by examiner

METHOD AND APPARATUS FOR DETECTING WEAR IN COMPONENTS OF HIGH VOLTAGE ELECTRICAL EQUIPMENT

This application is a continuation-in-part of prior application Ser. No. 10/241,108 filed Sep. 11, 2002, now U.S. Pat No. 6,777,948, which is incorporated by reference herein in its entirety.

BACKGROUND OF THE INVENTION

1. Field of the Invention

The invention relates generally to high voltage electrical equipment. More specifically, the invention is directed to detecting wear in components of high voltage electrical equipment that are regularly exposed to electrical arcing.

2. Description of Related Art

Load tap changers, voltage regulators, circuit breakers and switches are used to interrupt power. The surfaces of some of their components are eroded by being regularly exposed to electrical arcing and mechanical friction during the course of their normal operation. Equipment failure results if these components are allowed to wear out to the extent that their electrical and mechanical integrity is compromised. Components most susceptible to erosion are the arcing metal contacts and TEFLON nozzles in sulfur hexafluoride ($SF_6$) gas circuit breakers.

It is desirable to know when components of electrical equipment have become dangerously worn out without taking the equipment out of service to perform an internal inspection. Several approaches have been used to accomplish this. One approach is installing fiber optic strands into the electrical contacts of the electrical equipment. As the contacts wear, the fiber optic strands become exposed to light emitted from electrical arcing, which may be detected by a photodiode or other sensor placed at the opposite ends of the fiber optic strands. Installing fiber optic strands in electrical contacts is expensive, however, and the fiber optic strands are subject to breakage as a result of mechanical stress. Another approach embeds tracer materials at predetermined depths in the electrical contacts or below the surface of a TEFLON nozzle of a $SF_6$ circuit breaker. When the electrical contacts wear to the point that the tracer materials are exposed, the tracer materials are released into the insulating medium or else are decomposed by the electrical arc. In order to determine whether wear has proceeded beyond a safe level, the insulating medium must be withdrawn and analyzed periodically for the presence of the tracer elements or the products from their decomposition. This approach is not suitable for continuous monitoring of the electrical equipment.

Based on the foregoing, there is a need for a way to continuously monitor for excessive wear of the components of electrical equipment that are susceptible to erosion by being exposed to electrical arcing and mechanical friction. In addition, there is a need for new tracer materials and methods of analyzing these materials.

SUMMARY OF THE INVENTION

Accordingly, it is an object of the present invention to detect excessive wear in components of electrical equipment by monitoring them continuously.

This object and other objects are provided by the present invention, one embodiment of which comprises a method of monitoring a component of an electrical device for wear by exposing a component having a tracer material embedded in it at a predetermined depth to an electrical arc, wearing the component until the tracer material is exposed to the electrical arc, and detecting electromagnetic radiation emitted by the tracer material when the tracer material is exposed to the electrical arc. The electromagnetic radiation emitted by the tracer material is distinct from electromagnetic radiation emitted by any other parts of the component; for example, it may have a different wavelength. The component is preferably monitored continuously to detect electromagnetic radiation emitted by the tracer material. Another embodiment of the present invention comprises a method of manufacturing a component of a device in which an electrical arc may be generated wherein the method involves embedding a tracer material within the component at a predetermined depth.

Yet another embodiment of the present invention comprises an apparatus for detecting wear in an electrical device in which a tracer material is embedded at a predetermined depth within a component of the electrical device. As in the other embodiments, the tracer material emits electromagnetic radiation when the tracer material is exposed to an electrical arc that is distinct from electromagnetic radiation emitted by any other parts of the component; for example, it may have a different wavelength. The apparatus preferably includes an electromagnetic detector, such as a photodiode having a narrow bandwidth filter or spectrophotometer, to continuously monitor the component for electromagnetic radiation emitted by the tracer material. A fiber optic cable may be used to transmit the electromagnetic radiation to the electromagnetic detector. Suitable tracer materials include lithium, cobalt, niobium and rare earth metals, such as yttrium. In addition, multiple tracer materials may be embedded at multiple pre-determined depths and/or at preselected locations within the component in order to detect the extent and/or location of wearing in the component.

In another embodiment, the present invention provides a method for detecting wear in a component of an electrical device, comprising exposing a component of an electrical device to an electrical arc, wherein the component has a fluorescent tracer material embedded at a predetermined depth; wearing the component such that the fluorescent tracer material is released into an insulating medium surrounding at least a portion of the component; irradiating the insulating medium, thereby causing the fluorescent tracer material to produce fluorescence; and detecting the fluorescence from the fluorescent tracer material.

In another embodiment, the present invention provides a method for manufacturing a component of a device in which an electrical arc may be generated, comprising embedding a fluorescent tracer material in a component of a device at a predetermined depth. The present invention also provides a system for detecting wear in an electrical device, comprising a component of a device that is exposed to an electrical arc, wherein the component is insulated by an insulating medium; a fluorescent tracer material embedded at a predetermined depth in the component; and a detector configured to irradiate the fluorescent tracer material and to detect fluorescence produced by the fluorescent tracer material.

These and other objects and features of the invention will appear from the following description from which the preferred embodiments are set forth in detail in conjunction with the accompanying drawings.

DETAILED DESCRIPTION OF THE PREFERRED EMBODIMENTS

The structure and function of the preferred embodiments can best be understood by reference to the drawings. The reader will note that the same reference designations appear in multiple locations. Where this is the case, the numerals refer to the same or corresponding structure in those locations.

Figure 1:
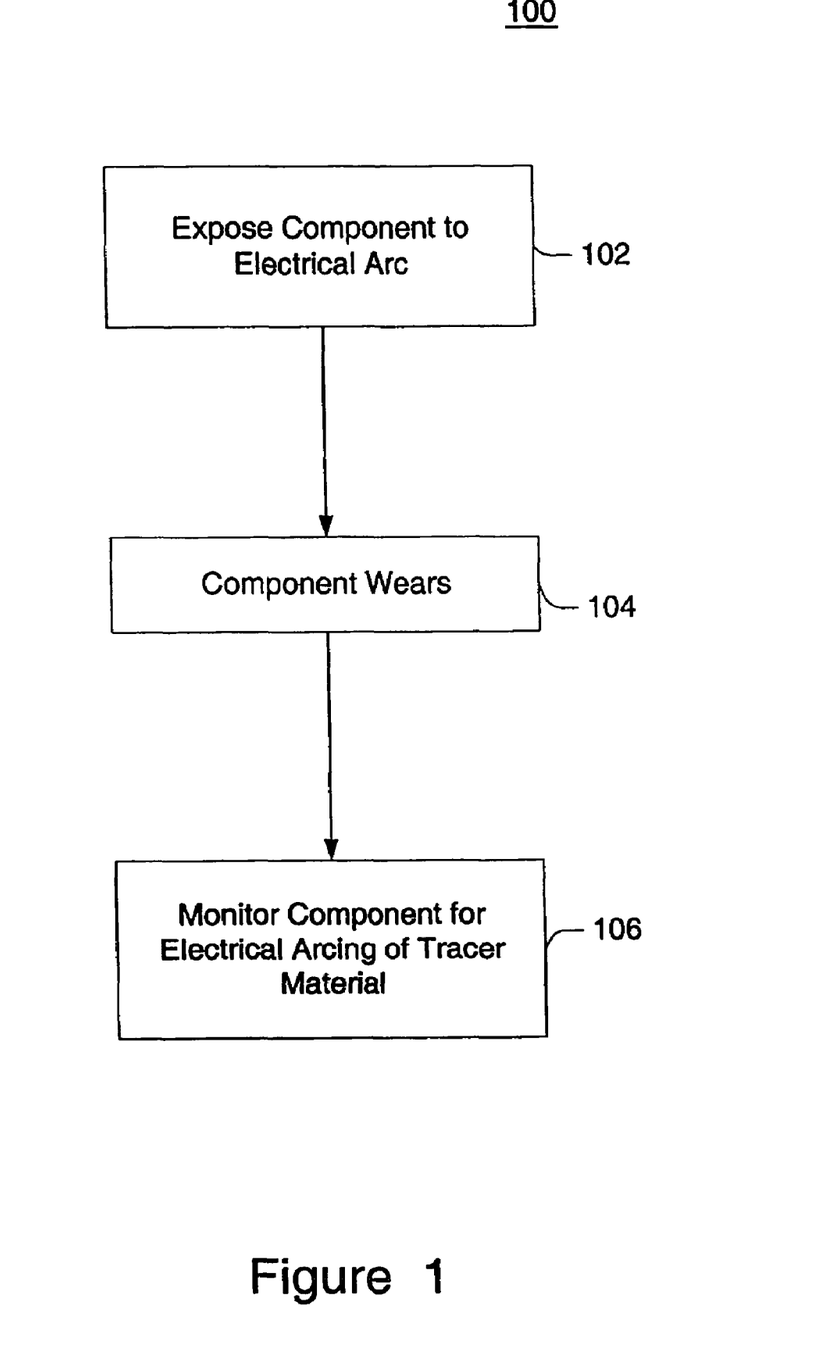
FIG. 1 is a flowchart of a method for detecting wear in a component of an electrical device in accordance with an embodiment of the invention.

FIG. 1 shows a flowchart 100 for detecting wear in a component of an electrical device in accordance with an embodiment of the present invention. In step 102 the component, which contains a tracer material embedded in it at a predetermined depth, is exposed to an electrical arc. In step 104 the component wears as a result of the exposure to the electrical arc or other causes, such as mechanical friction. Lastly, the component is continuously monitored for electromagnetic radiation from the tracer material in step 106; the tracer material emits electromagnetic radiation when the component is sufficiently worn so that the embedded tracer material itself is exposed to the electric arc. The tracer material is embedded in the component preferably during the manufacturing of the component, but the tracer material may also be embedded in existing components after they have been manufactured.

Figure 2:
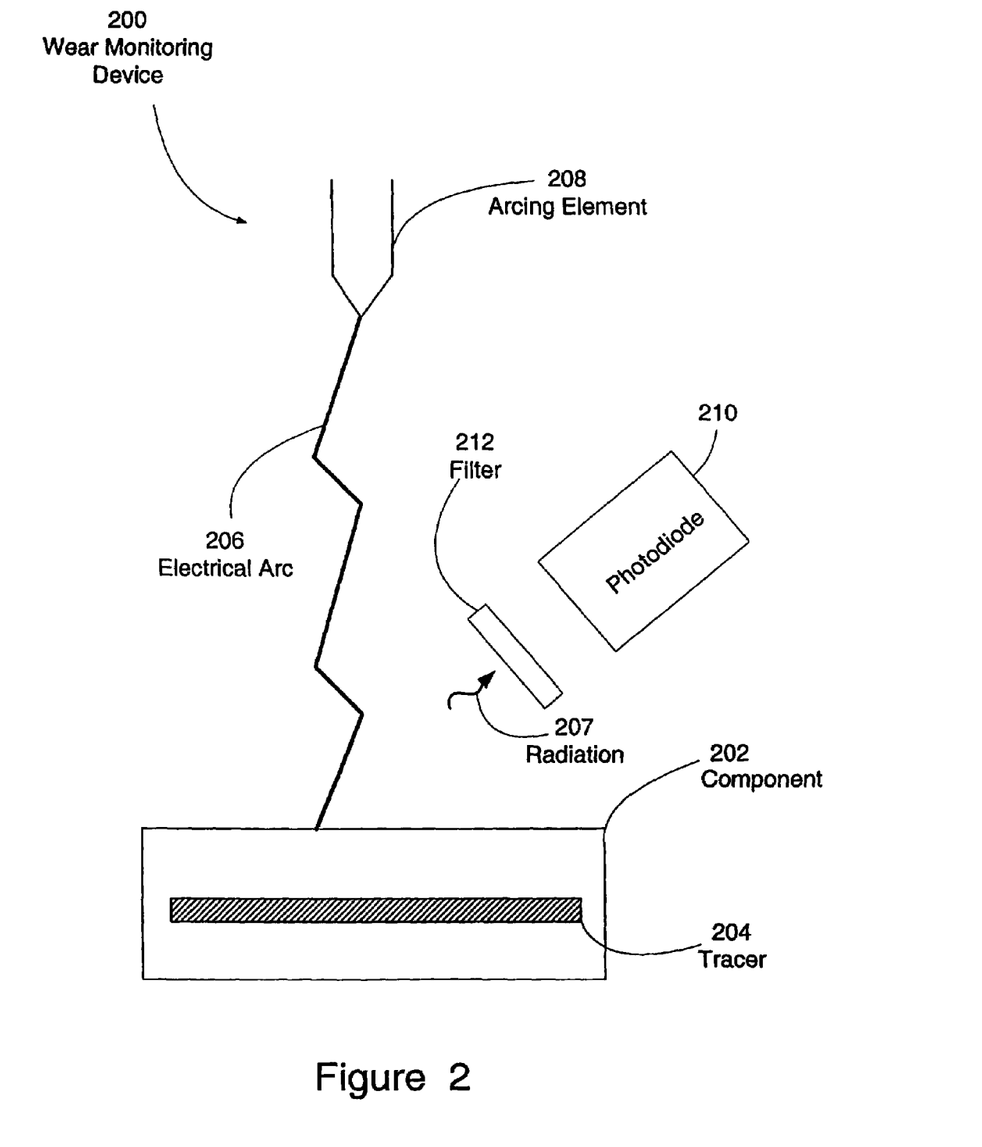
FIG. 2 is a schematic of an apparatus for detecting wear in a component of an electrical device in accordance with an embodiment of the invention.
Figure 3:
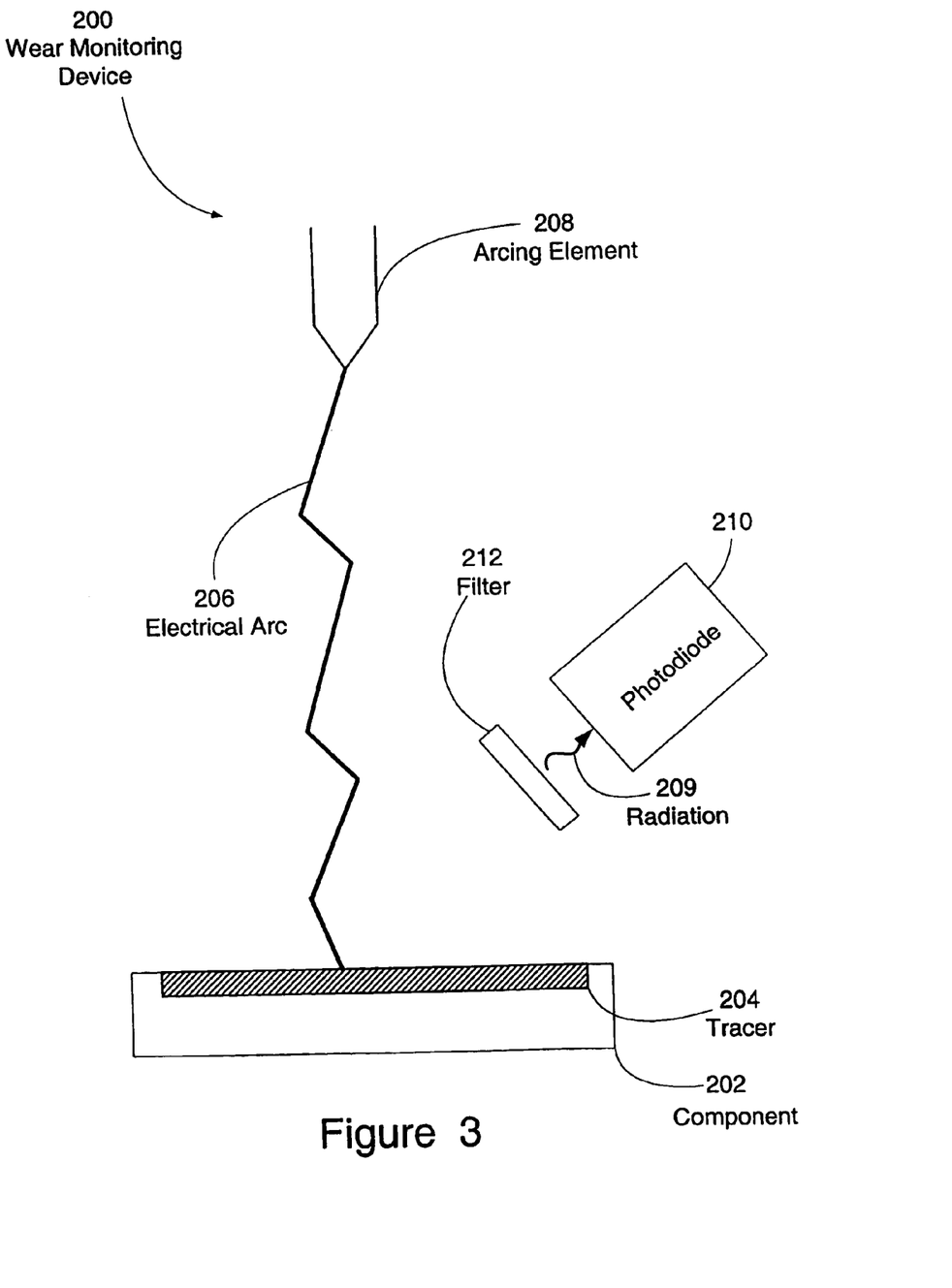
FIG. 3 is a schematic of the apparatus in FIG. 2 at a later time after the component has been worn to expose a tracer material.

FIGS. 2 and 3 are schematics of an apparatus 200 for detecting wear in a component 202 of an electrical device in accordance with an embodiment of the present invention. FIG. 2 illustrates the apparatus 200 at an initial time, and FIG. 3 illustrates the apparatus at a later time. As shown in FIG. 2, a component 202 of an electrical device (not shown) has a tracer material 204 embedded in it at a predetermined depth. The component 202 is exposed to an electrical arc 206 that is generated by an electrical arcing element 208. The high temperature of the electrical arc 206 causes the portion of the component 202 that is exposed to the electrical arc 206 to emit electromagnetic radiation 207 that is continuously monitored by an electromagnetic detector, which may be a photodiode 210 or any other suitable detector for electromagnetic radiation (such as a spectrophotometer). In the embodiment shown in FIG. 2, a narrow band filter 212 is placed between the photodiode 210 and the component 202 of the electrical device so that the photodiode 210 is allowed to detect electromagnetic radiation having a wavelength in the narrow band that can pass through the narrow band filter 212. As shown in FIG. 2, the electromagnetic radiation 207 has not been transmitted through the narrow band filter 212 because the electromagnetic radiation 207 was not emitted by the tracer material 204. The electromagnetic detector is capable of monitoring the component 202 of the electrical device continuously during the operation of the electrical device.

FIG. 3 is a schematic of the apparatus 200 in FIG. 2 but at a later time after the component 202 has been worn. In contrast to FIG. 2, FIG. 3 shows the tracer material 204 on a surface of the component 202, instead of embedded in the component at a predetermined depth. At the later time illustrated in FIG. 3, the surface of the component 202 has been worn away as a result of exposure to the electrical arc 206 or other causes, such as mechanical friction, so that the tracer material 204 is exposed to the electrical arc 206. The high temperature of the electrical arc 206 causes the tracer material 204 to emit electromagnetic radiation 209. The tracer material 204 is selected so that when it is exposed to the electrical arc 206, it emits electromagnetic radiation 209 that is distinct from the electromagnetic radiation 207 (FIG. 2) emitted by any other parts of the component that are exposed to the electrical arc. For example, lithium, which emits red light corresponding to a wavelength of approximately 670.7 nm, may be a suitable tracer material in some applications. It is desirable for the tracer material 204 to be chemically and thermally stable under the operating conditions for the component. It may also be desirable for the tracer material 204 not to affect the dielectric properties of any fluid medium in the electrical device in which it is to be used. Among the materials that may be suitable for use as a tracer material in accordance with this invention are lithium, cobalt, niobium and rare earth metals such as yttrium. As shown in FIG. 3, the electromagnetic radiation 209 has been transmitted through the narrow band filter 212 because the electromagnetic radiation 209 was emitted by the tracer material 204.

In the embodiment shown in FIGS. 2 and 3, the electromagnetic radiation emitted by the tracer material 204 when it is exposed to the electrical arc 206 is detected by a photodiode 210 after the electromagnetic radiation has passed through a narrow band filter 212. The narrow band filter removes electromagnetic radiation with a wavelength outside the narrow band that is transmitted by the narrow band filter 212. The narrow band filter 212 is selected so that it transmits electromagnetic radiation that is emitted by the tracer material when it is exposed to the electrical arc but not electromagnetic radiation emitted by other parts of the component 202.

Figure 4:
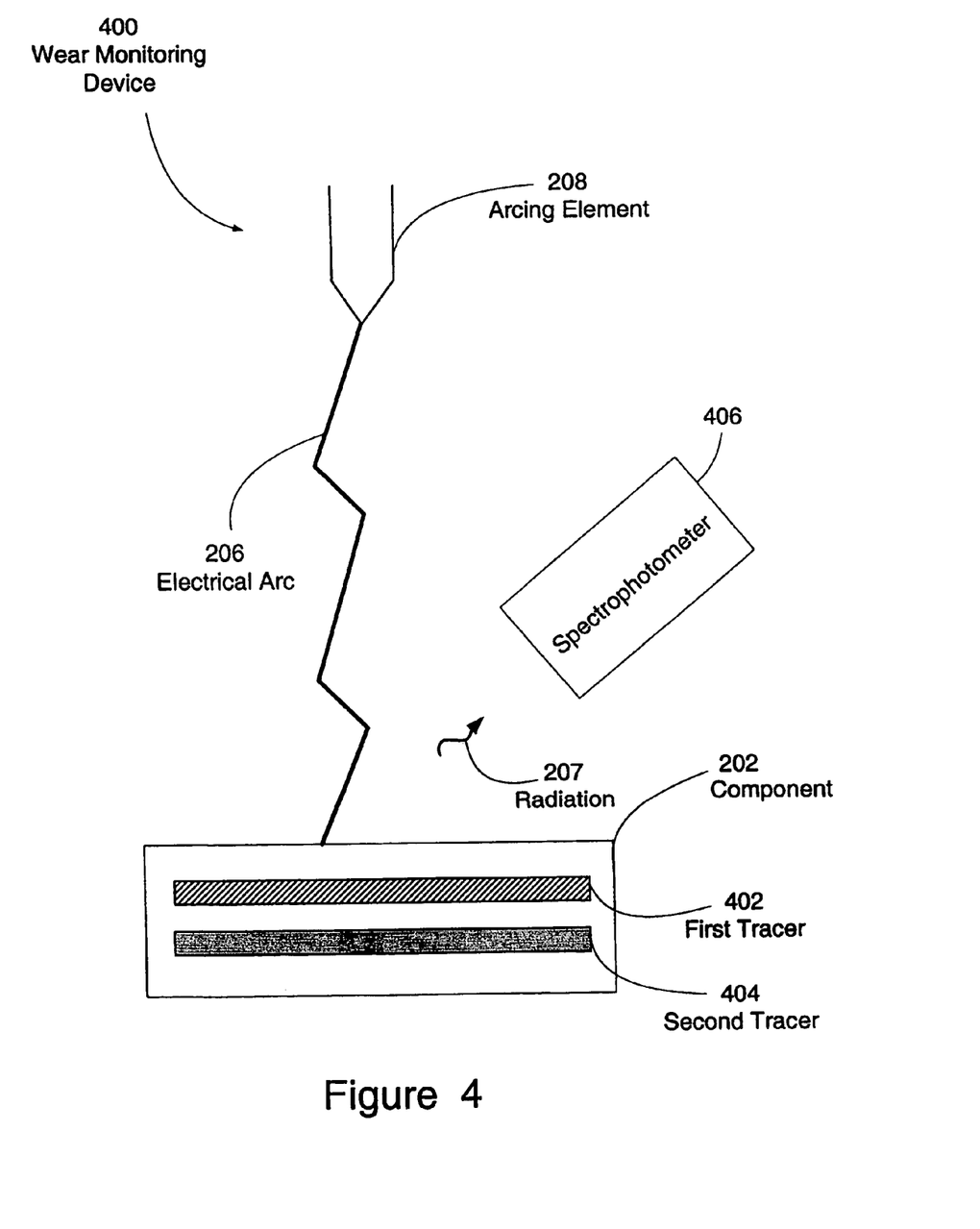
FIG. 4 is a schematic of an apparatus for detecting two amounts of wear in a component of an electrical device in accordance with an alternate embodiment of the invention.

FIG. 4 is a schematic of an apparatus 400 for detecting two amounts of wear in a component 202 of an electrical device in accordance with an alternate embodiment of the present invention. As shown in FIG. 4, a first tracer material 402 is embedded at one depth within the component 202 and a second tracer material 404 is embedded at another depth within the component 202. The first tracer material 402 and the second tracer material 404 are selected so that when they are exposed to the electrical arc 206, they emit electromagnetic radiation that is distinct from each other as well as from the radiation emitted by any other parts of the component that are exposed to the electrical arc. A spectrophotometer 406 analyzes electromagnetic radiation from the component 202 to determine whether the surface of the component 202 has worn to expose either the first tracer material 402 or the second tracer material 404. Alternatively, two photodiodes with differing narrow band filters may be used to monitor electromagnetic radiation from the first tracer material 402 and the second tracer material 404. Additional tracer materials (not shown) may be imbedded in the component 202 at various depths and/or at different locations in order to estimate the extent and/or location of wear of the component 202 according to which of the tracer materials is exposed to the electrical arc 206.

Figure 5:
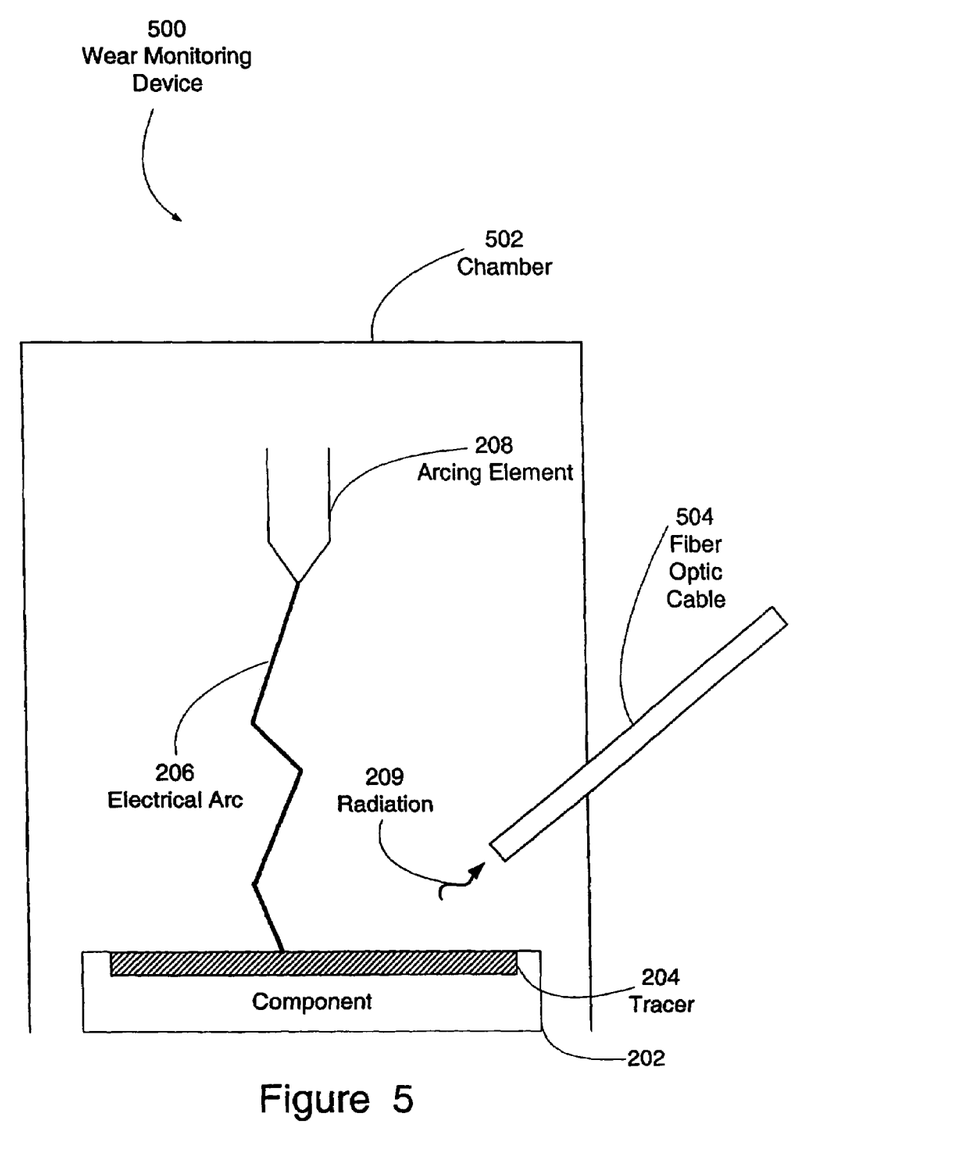
FIG. 5 is a schematic of an apparatus for detecting wear in a component of an electrical device in accordance with an alternate embodiment of the invention.

FIG. 5 is a schematic of an apparatus 500 for detecting wear in a component 202 of an electrical device in accordance with an alternate embodiment of the present invention. In the embodiment shown in FIG. 5, an arcing element 208 and a component 202 having an embedded tracer material 204 are placed in an equipment chamber 502 and a fiber optic cable 504 is used to transmit electromagnetic radiation emitted by the component to an electromagnetic detector (not shown) outside the equipment chamber 502.

The invention having been described, the following are examples of use of the present invention and are presented to illustrate, rather than to limit the scope of the invention. The following examples illustrate a apparatus for detecting wear in a load tap changer and a circuit breaker according to the present invention. Other equipment in which this invention could be used include voltage regulators and $SF_6$ gas circuit breakers.

Figure 6:
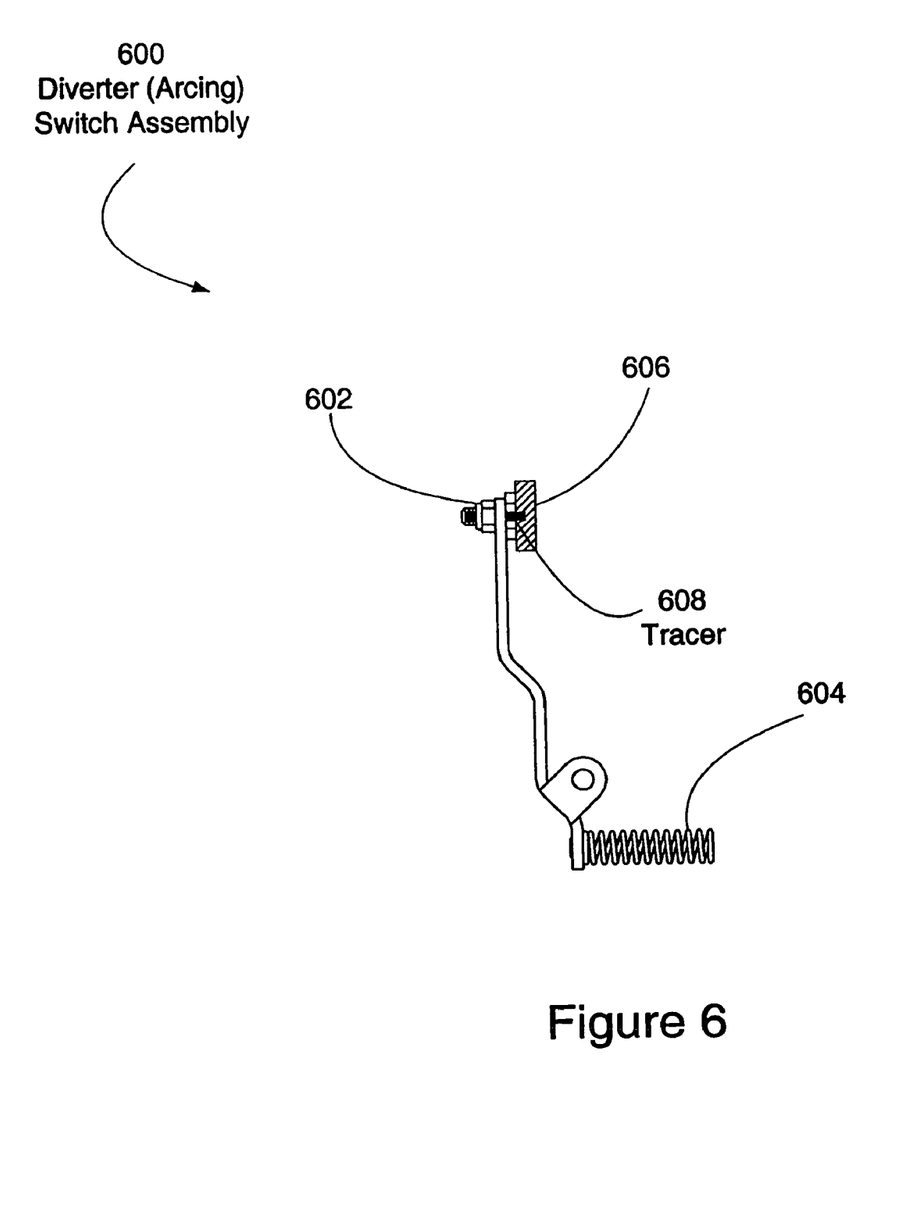
FIG. 6 is a diagram showing a cross-sectional view of components of a load tap changer in accordance with an embodiment of the invention.

FIG. 6 is a cross-sectional view of a diverter switch assembly 600 of a load tap changer in accordance with an embodiment of the invention. The diverter switch assembly 600 includes an arcing contact tip assembly 602 at one end of the diverter switch assembly and a compression spring 604 at its opposite end. The arcing contact tip assembly 602 may include an elkonite contact 606. As shown in FIG. 6, tracer material 608 is embedded within the elkonite contact 606. In accordance with the present invention, the tracer material 608 will become exposed to an electrical arc (not shown) after the surface of the elkonite contact 606 is worn away, and an electromagnetic detector (not shown) will detect the distinctive electromagnetic radiation emitted by the tracer material 608.

Figure 7:
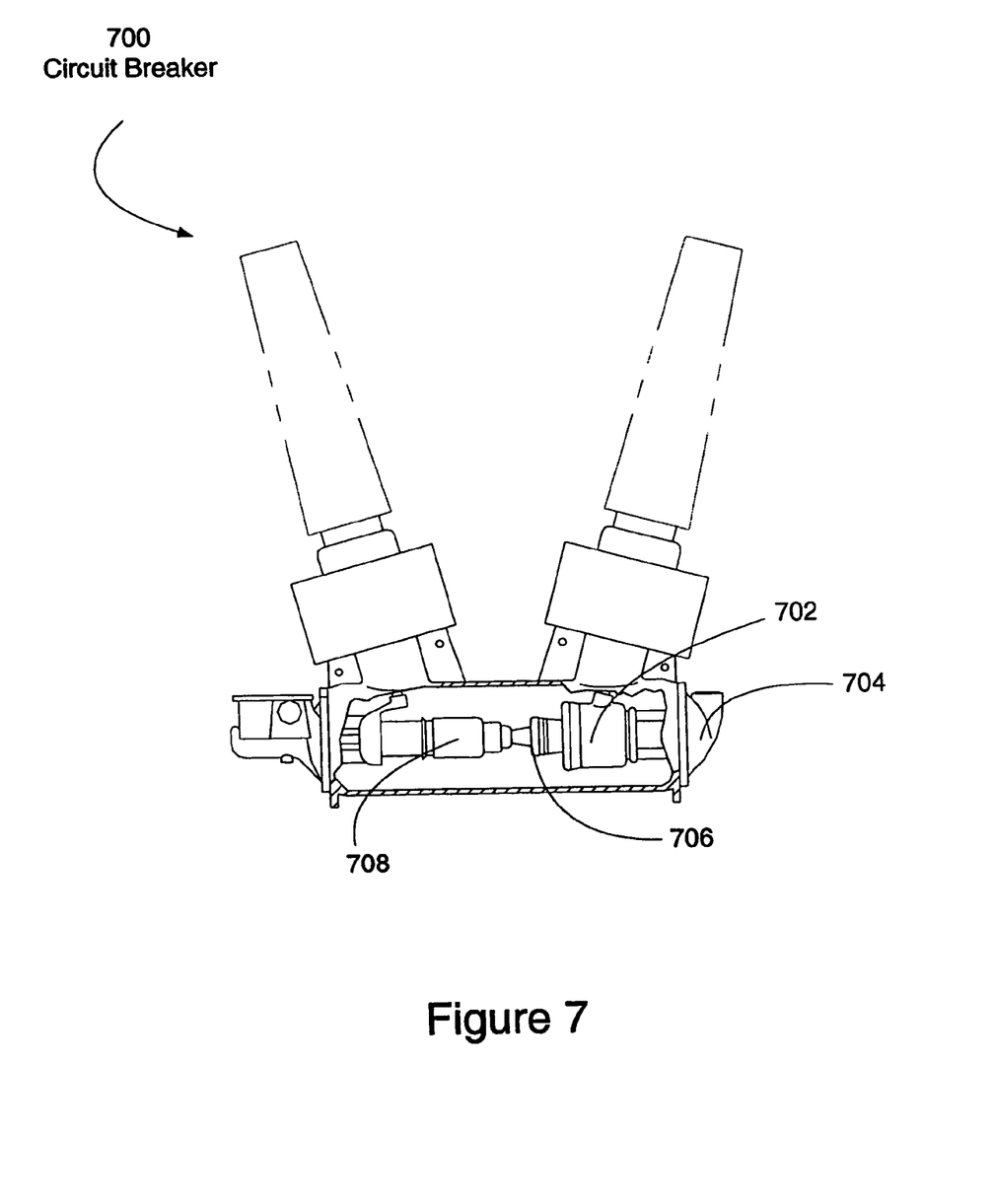
FIG. 7 is a diagram showing a partially cut away cross-sectional view of components of a circuit breaker in accordance with an embodiment of the invention.
Figure 8:
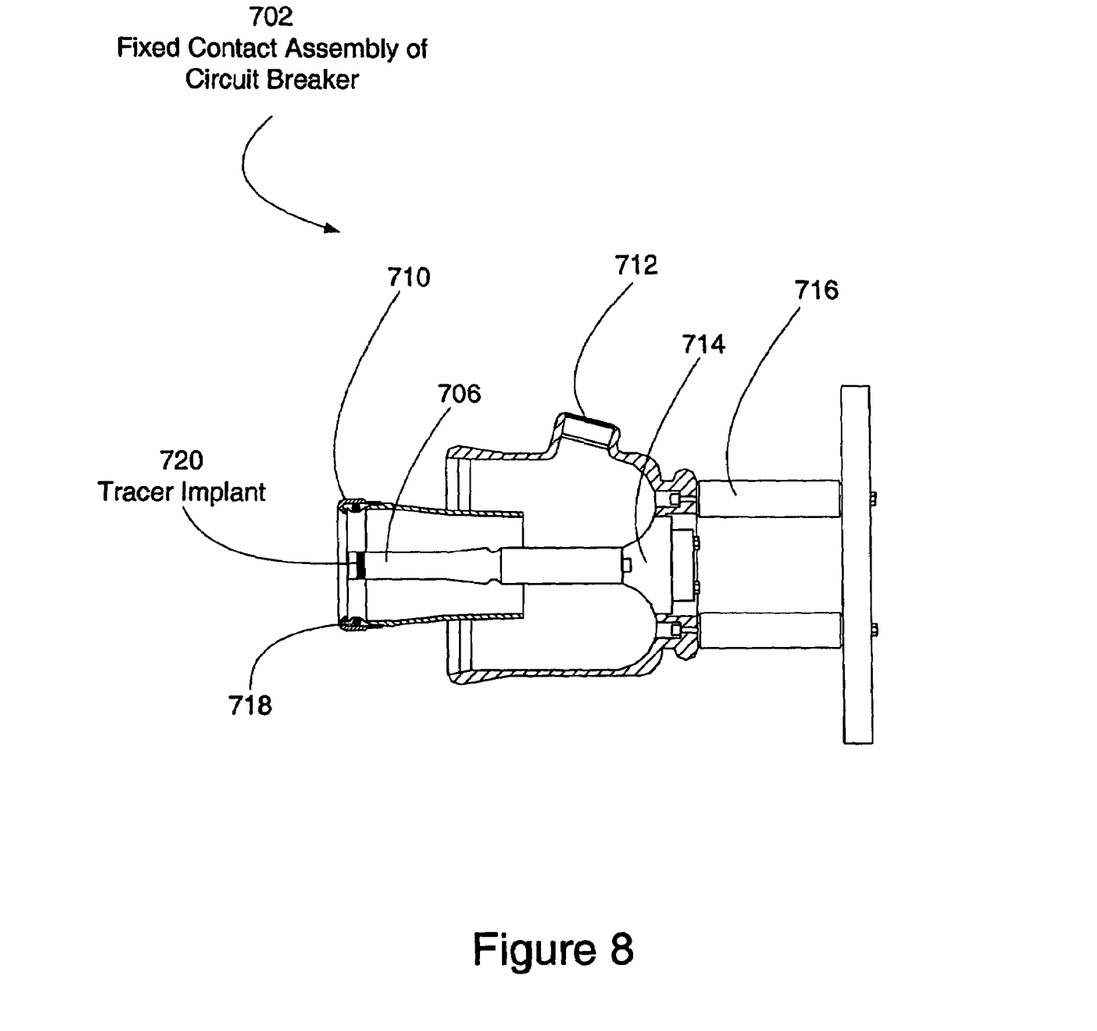
FIG. 8 is a diagram showing a partially cut away cross-sectional view of the fixed contact assembly of a circuit breaker in accordance with an embodiment of the invention.
Figure 9:
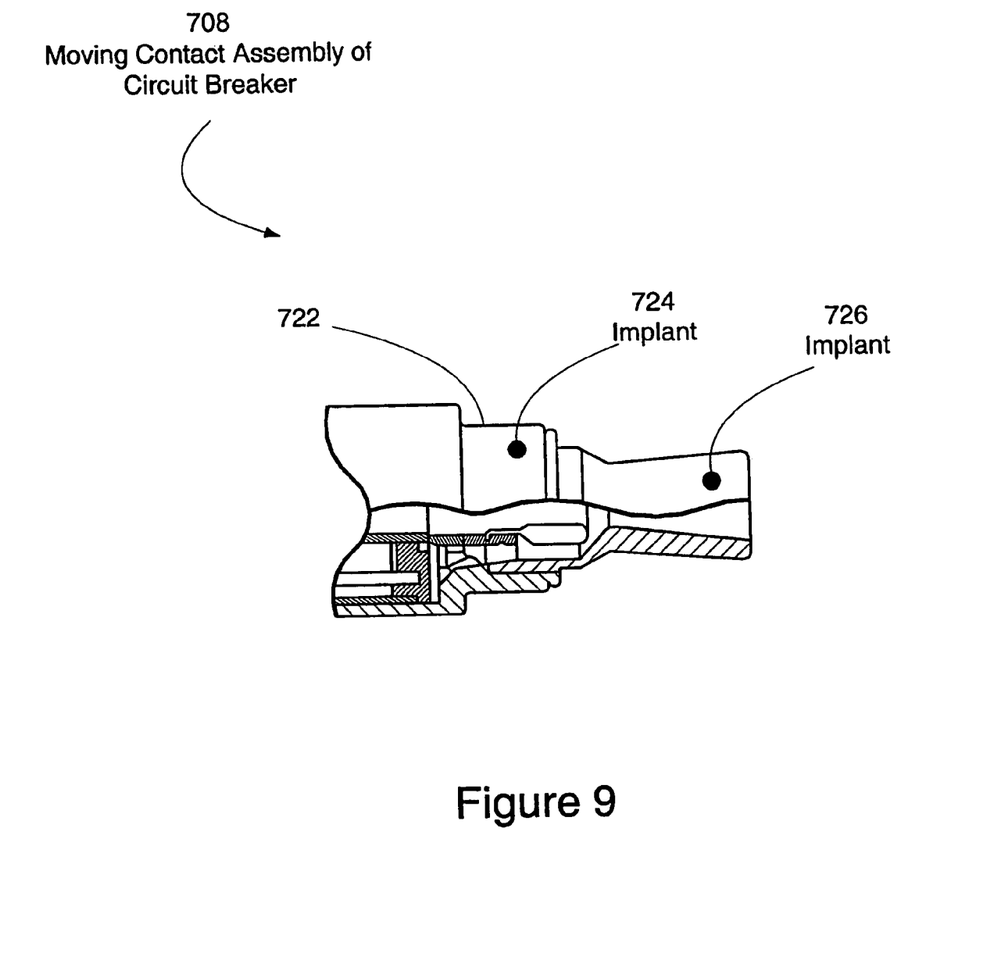
FIG. 9 is a diagram showing a partially cut away cross-sectional view of the moving contact assembly of a circuit breaker in accordance with an embodiment of the invention.

FIGS. 7, 8 and 9 are, respectively, partially cut away cross-sectional views of a circuit breaker 700, the fixed contact assembly 702 of the circuit breaker 700, and the moving contact assembly 708 of the circuit breaker 700 in accordance with an embodiment of the invention. FIG. 7 shows a circuit breaker 700, comprised of a fixed contact assembly 702 with a fixed contact pin 706, a tank 704, and a moving contact assembly 708.

FIG. 8 shows a fixed contact assembly 702 of a circuit breaker 700, comprised of shielding 710, a multicontact liner and a clamping ring 712, a contact pin holder 714, insulating support 716, a contact crown 718, and a fixed contact pin 706. As shown in FIG. 8, tracer material 720 is embedded within the fixed contact pin 706. In accordance with the present invention, the tracer material 720 will become exposed to an electrical arc (not shown) after the surface of the fixed contact pin 706 is worn away, and an electromagnetic detector (not shown) will detect the distinctive electromagnetic radiation emitted by the tracer material 720.

FIG. 9 shows a moving contact assembly 708 of a circuit breaker 700, comprised of a main contact 722. As shown in FIG. 8, tracer materials 724 and 726 are embedded within the main contact 722. In accordance with the present invention, the tracer materials 724 and 726 will become exposed to an electrical arc (not shown) after the surface of the main contact 722 is worn away, and an electromagnetic detector (not shown) will detect the distinctive electromagnetic radiation emitted by the tracer materials 724 and 726.

Figure 10:
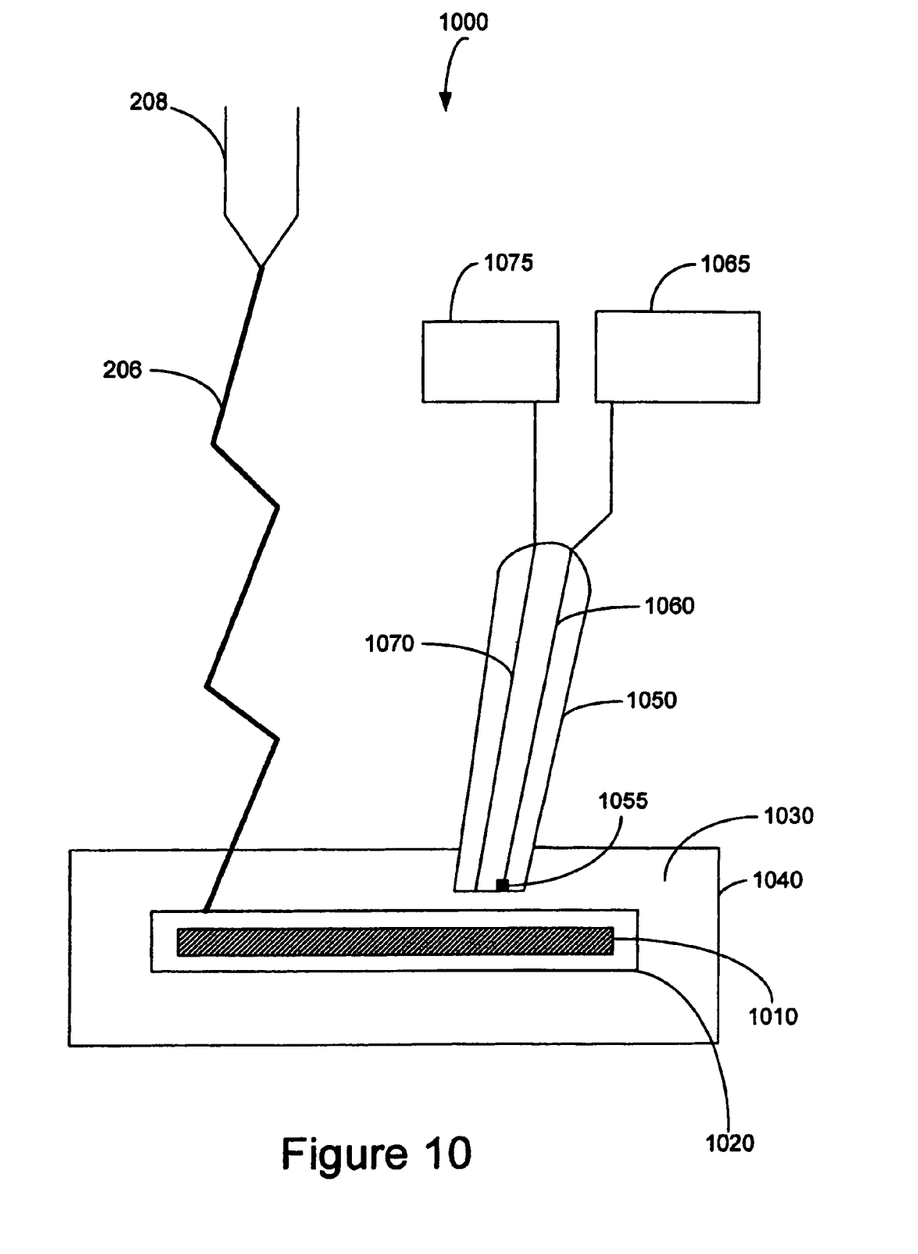
FIG. 10 provides a schematic of an apparatus for detecting wear in a component of an electrical device in accordance with another embodiment of the invention.

FIG. 10 provides a schematic of an apparatus 1000 for detecting wear in a component of an electrical device in accordance with another embodiment of the invention. In this embodiment, the tracer material 1010 comprises a fluorescent material. The fluorescent material is embedded at a predetermined depth in a component 1020 of an electrical device. This embodiment is preferably used when the component 1020 is immersed in an insulating medium 1030, such as a mineral oil. The insulating medium preferably surrounds the component 1020 and is contained within a container 1040 or the electrical device within which the component 1020 resides. When the component 1020 becomes sufficiently worn down, the fluorescent tracer material 1010 becomes exposed and is released into the insulating medium 1030. As shown in FIG. 10, the wear of the component 1020 may be the result of an arc 206 that is discharged from an arcing element 208 or may be the result of mechanical friction.

Once the fluorescent tracer material 1010 is released, the insulating medium 1030 is irradiated or illuminated, thereby exciting the fluorescent tracer material 1010 and causing it to fluoresce. In this embodiment, a probe 1050 is disposed in the container 1040 or electrical device holding the insulating medium and is used to provide radiation or excitation light to the insulating medium 1030. A radiation or electromagnetic radiation source 1075 is connected to the probe by, for example, a fiber optic connection 1070, which supplies radiation to the insulating medium 1030. The radiation source 1075 may be any source of light or radiation having a desired wavelength corresponding to the wavelength necessary to cause the fluorescent tracer material 1010 in the insulating medium 1030 to fluoresce. Preferably, the wavelength of the fluorescence is different from the light used to irradiate or illuminate the fluorescent tracer material.

The fluorescence produced by the fluorescent tracer material 1010 that has been irradiated or illuminated by the radiation from the probe 1050 is also detected by the same probe 1050. In this case, the probe 1050 also comprises a detector 1055, such as an optical sensor, such as a photodiode, or other suitable device, that may continuously monitor for and detect fluorescence. It should be appreciated that other optical elements, such as filters, may be used in conjunction with the detector 1055 to selectively monitor for specific fluorescence produced by the irradiated fluorescent tracer material 1010 in the insulating medium 1030. The detector 1055 is electrically connected by an electrical connector 1060 to a recording device 1065 that will record and analyze the signal provided by the detector 1055 to determine whether the fluorescent tracer material 1010 has been released into the insulating medium 1030, thereby indicating that wear of the component 1020 has progressed to a predetermined amount. Alternatively, the detector 1055 may simply be the end of a fiber optic cable that passes received light to an optical monitoring device, such as a spectrophotometer, for analysis (not shown).

It should be appreciated that, in this embodiment, the probe may be permanently positioned within the insulating medium 1030 to irradiate, in-situ, any fluorescent tracer material released into the insulating medium and to detect, in-situ, fluorescence on a continuous, semi-continuous or as-needed basis. Preferably, fluorescence is detected during a time when there is no arcing so as to minimize any interference that may be caused by the arc in detecting the fluorescence. Alternatively, the container 1040 may be configured such that the probe 1050 can be inserted only when needed. In addition, it should be appreciated that the signal provided by the detector 1055 or by an optical monitoring device, such as a spectrophotometer, can also be connected to a computer for data storage and analysis. Further, it should be appreciated that the fluorescent tracer material may be utilized at any desired depth within the component and may be placed at more than one depth within the same component, thereby providing information regarding the rate of deterioration of the component and multiple indications as the component wears.

The fluorescent tracer material itself may be any fluorescent material; provided that it will either dissolve in, or disperse in, the surrounding insulating medium. Preferably, the fluorescent tracer material will provide enough fluorescence such that, upon dissolving or dispersing in the surrounding insulating medium, such fluorescence can be detected at low concentrations of the fluorescent tracer material in the insulating medium. In one embodiment, fluorescence from the fluorescent material should be detectable at a concentration of approximately 0.5 ppb of the fluorescent material in the insulating material. Preferably, upon excitation from a light or energy source, the fluorescent tracer material emits a light (i.e., fluorescence) that has a wavelength that is always longer than that of the excitation light (such as ultraviolet or visible light). When the insulating material is an oil, it is desirable to select a fluorescent tracer material that emits light or fluorescence in the red region of the spectrum to minimize interference from the oil.

The composition of the fluorescent material may be an organic dye. Any suitable organic dye may be used. The organic dye can be a powder or a liquid containing the organic dye powder. If the organic dye is in liquid form, the liquid can be sealed in a container within the electrical component in which it is embedded; however, the container must be capable of rupturing once it is exposed to allow the organic dye to dissolve or disperse into the surrounding insulating medium. Preferably, the organic dye has a high solubility in the insulating medium such as oil, good chemical and thermal stability, a high boiling point, for example, a boiling point greater than approximately 150° C., and the ability to produce a high level of fluorescence. In one embodiment, the organic dye is a solvent dye, including, for example, azo dyes, which is more soluble in the insulating medium and will not settle out.

The fluorescent material may also be an inorganic nanocrystal powder. Preferably, the inorganic nanocrystal powder is a semiconductor nanocrystal quantum dot, ranging in a particulate size from approximately 2–10 nm, with a preferred size range of approximately 4–5 nm. These types of nanocrystals typically exhibit high fluorescence intensity in a narrow bandwidth, are very chemically and thermally stable, are resistive to fading, and can be excited with a broadband source. In a preferred embodiment, the nanocrystal powder may be cadmium-tellurium/cadmium sulfide or cadmium-selenium/zinc sulfide, such as EVIDOTS, available from Evident Technology. These specific nanocrystals also emit light in the red region of the spectrum and are prone to less interference from the insulating medium such as oil.

Figure 11:
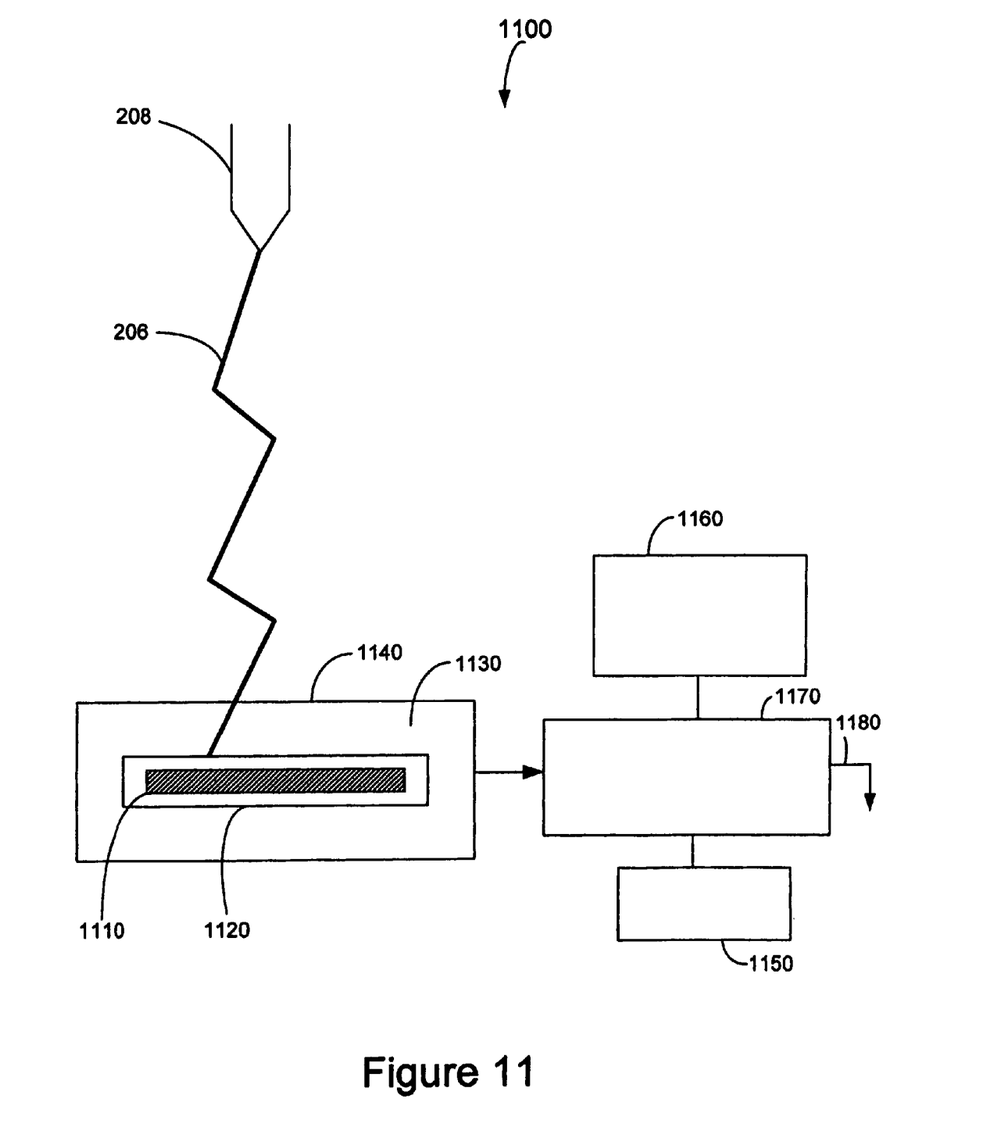
FIG. 11 provides a schematic of an apparatus for detecting wear in a component of an electrical device in accordance with yet another embodiment of the invention.

FIG. 11 provides a schematic of an apparatus 1100 for detecting wear in a component of an electrical device in accordance with yet another embodiment of the invention. As in FIG. 10, the tracer material 1110 comprises a fluorescent material that is embedded at a predetermined depth of the component 1120, where the component 1120 is immersed in an insulating medium 1130, such as a mineral oil, that is disposed in a container 1140. When the component 1120 becomes sufficiently worn down, such as wear resulting an electrical arc 206 that is discharged from an arcing element 208, or from mechanical wear, the fluorescent tracer material 1110 is exposed and released into the insulating medium 1130. The fluorescent tracer material may be any of the materials previously described in connection with FIG. 10. In this embodiment, however, irradiation or excitation of the fluorescent tracer material 1110 that has been released into the surrounding insulating medium 1130, and detection of the resulting fluorescence occurs outside of the electrical component and device.

Specifically, the insulating medium surrounding the component is fluidly connected to a sample cell. Therefore, a sample of the insulating medium 1130 is taken from the container 1140 and passed to a sample cell 1170 for analysis. It should be appreciated that the sampling rate and amount may be computer-controlled.

The sample in the sample cell 1170 is irradiated or excited using radiation from a radiation or electromagnetic source 1150 at a wavelength that corresponds to the wavelength in which the particular fluorescent tracer material fluoresces. A detector 1160, such as a spectrophotometer or similar analytical device, can be used to detect the resulting fluorescence. Generally, the sample is discarded after irradiation and detection through a discharge line 1180. It should be appreciated that sampling may be done on an as-needed basis, including semi-continuously or continuously. The sample size will generally be only a few milliliters of insulating material; however, depending upon the sampling frequency, additional insulating medium may need to be added to the insulating medium surrounding the component. Alternatively, the sample may be returned to the insulating medium surrounding the component; however, in this case, a baseline or background signal should be established before exciting the next sample to compensate for residual fluorescent tracer material that has been returned.

It should be appreciated that similarly to FIG. 10, the detector 1160 may be coupled to a computer for storage and analysis of the collected data. It should also be appreciated that sampling of the insulating medium may be done manually, thereby avoiding the need to fluidly connect the sample cell to the insulating medium surrounding the component.

Various embodiments of the invention have been described. The descriptions are intended to be illustrative of the present invention. It will be apparent to one of skill in the art that modifications may be made to the invention as described without departing from the scope of the claims set out below. For example, it is to be understood that although the invention has been described using a photodiode with a narrow band filter as an example of an electromagnetic radiation detector, any suitable electromagnetic radiation detector may be used by the present invention. Furthermore, it is to be understood that although the invention has been illustrated with particular examples of a load tap changer and a circuit breaker, any component of electrical equipment that is exposed to an electrical arc is contemplated to fall within the scope of the invention.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are therefore to be considered in all respects as illustrative and not restrictive, the scope of the invention being indicated by the appended claims, and not limited to the foregoing description.

What is claimed is:

1. A method for detecting wear in a component of an electrical device, comprising:
   exposing a component of an electrical device to an electrical arc, wherein the component has a fluorescent tracer material embedded at a predetermined depth;
   wearing the component such that the fluorescent tracer material is released into an insulating medium surrounding at least a portion of the component;
   irradiating the insulating medium, thereby causing the fluorescent tracer material to produce fluorescence; and
   detecting the fluorescence from the fluorescent tracer material.

2. The method of claim 1 further comprising sampling the insulating medium to produce a sample of the insulating medium and wherein the sampling occurs before the irradiating.

3. The method of claim 2, wherein the sampling comprises sampling the insulating medium at predetermined intervals.

4. The method of claim 2, wherein the sampling comprises passing the sample to a sample cell.

5. The method of claim 4, wherein the irradiating and the detecting are performed on the insulating medium in the sample cell.

6. The method of claim 1, wherein the irradiating comprises irradiating the insulating medium in-situ.

7. The method of claim 6, wherein the detecting comprises detecting the fluorescence in-situ.

8. The method of claim 1, wherein the irradiating comprises irradiating the insulating medium with ultraviolet light.

9. The method of claim 1, wherein the irradiating comprises irradiating the insulating medium with visible light.

10. The method of claim 1, wherein the fluorescent tracer material comprises an organic dye.

11. The method of claim 1, wherein the fluorescent tracer material comprises an inorganic nanocrystal powder.

12. The method of claim 11, wherein the inorganic nanocrystal powder comprises cadmium selenium-zinc sulfide.

13. A system for detecting wear in an electrical device, comprising:
    a component of a device that is exposed to an electrical arc, wherein the component is insulated by an insulating medium;
    a fluorescent tracer material embedded at a predetermined depth in the component; and
    a probe configured to irradiate the fluorescent tracer material and to detect fluorescence produced by the fluorescent tracer material.

14. The system of claim 13, wherein the fluorescent tracer material comprises an organic dye.

15. The system of claim 13, wherein the fluorescent tracer material comprises an inorganic nanocrystal powder.

16. The system of claim 15, wherein the inorganic nanocrystal powder comprises cadmium selenium-zinc sulfide.

17. The system of claim 13, further comprising:
    a detector housed within the probe;
    a recording device connected to the detector; and
    a radiation source connected to the probe.

18. The system of claim 13, wherein the probe is configured to be disposed within the insulating medium.

19. A system for detecting wear in an electrical device, comprising:
    a component of a device that is exposed to an electrical arc, wherein the component is insulated by an insulating medium;
    a fluorescent tracer material embedded at a predetermined depth in the component;
    a sample cell configured to receive a sample of the insulating medium;
    a radiation source configured to provide radiation to the sample cell; and
    a detector configured to detect fluorescence emitted from the sample cell.

20. The system of claim 19, wherein the fluorescent tracer material comprises an organic dye.

21. The system of claim 19, wherein the fluorescent tracer material comprises an inorganic nanocrystal powder.

22. The system of claim 21, wherein the inorganic nanocrystal powder comprises cadmium selenium-zinc sulfide.

23. A method for detecting wear in a component of an electrical device, comprising:
    exposing a component of an electrical device to an electrical arc, wherein the component has a fluorescent tracer material embedded at a predetermined depth;
    wearing the component such that the fluorescent tracer material is released into an insulating oil surrounding at least a portion of the component;
    irradiating the insulating oil in-situ, thereby causing the fluorescent tracer material to produce fluorescence; and
    detecting the fluorescence from the fluorescent tracer material in-situ.

24. The method of claim 23, wherein the irradiating comprises irradiating the insulating oil with ultraviolet light.

25. The method of claim 23, wherein the irradiating comprises irradiating the insulating medium with visible light.

26. The method of claim 23, wherein the fluorescent tracer material comprises an organic dye.

27. The method of claim 23, wherein the fluorescent tracer material comprises an inorganic nanocrystal powder.

28. The method of claim 27, wherein the inorganic nanocrystal powder comprises cadmium selenium-zinc sulfide.

* * * * *